(12) United States Patent  
Bilgic et al.

(10) Patent No.: US 9,336,611 B2  
(45) Date of Patent: May 10, 2016

(54) MULTI-CONTRAST IMAGE RECONSTRUCTION WITH JOINT BAYESIAN COMPRESSED SENSING

(75) Inventors: Berkin Bilgic, Cambridge, MA (US); Elfar Adalsteinsson, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 164 days.

(21) Appl. No.: 13/822,102

(22) PCT Filed: Sep. 13, 2011

(86) PCT No.: PCT/US2011/051309  
§ 371 (c)(1),  
(2), (4) Date: Mar. 25, 2013

(87) PCT Pub. No.: WO2012/037067  
PCT Pub. Date: Mar. 22, 2012

(65) Prior Publication Data  
US 2013/0188854 A1    Jul. 25, 2013

Related U.S. Application Data

(60) Provisional application No. 61/382,563, filed on Sep. 14, 2010.

(51) Int. Cl.  
*G06T 7/00* (2006.01)  
*G06T 11/00* (2006.01)  
*A61B 5/055* (2006.01)  
*A61B 5/00* (2006.01)  
*G01R 33/561* (2006.01)  
(Continued)

(52) U.S. Cl.  
CPC ............... *G06T 11/003* (2013.01); *A61B 5/055* (2013.01); *A61B 5/7264* (2013.01); *G01R 33/561* (2013.01); *G01R 33/5608* (2013.01); *G01R 33/4806* (2013.01); *G01R 33/5602* (2013.01); *G01R 33/5635* (2013.01); *G01R 33/56308* (2013.01); *G01R 33/56341* (2013.01)

(58) Field of Classification Search  
None  
See application file for complete search history.

(56) References Cited

U.S. PATENT DOCUMENTS

2004/0184648 A1 * 9/2004 Zhang et al. ............... 382/141  
2004/0234113 A1 * 11/2004 Miga ........................... 382/128  
(Continued)

OTHER PUBLICATIONS

Ji, Multitask Compressive Sensing, IEEE Transactions on Signal Processing, Jan. 2009, vol. 57, No. 1, pp. 92-106.*

(Continued)

*Primary Examiner* — Chan Park  
*Assistant Examiner* — Mai Tran  
(74) *Attorney, Agent, or Firm* — Quarles & Brady, LLP (57) ABSTRACT

A method for reconstructing multiple images of a subject depicting multiple different contrast characteristics from medical image data acquired with a medical imaging system is provided. Multiple image data sets are acquired with one or more medical imaging systems and the image data sets used to estimate hyperparameters drawn from a prior distribution, such as a prior distribution of image gradient coefficients. These hyperparameters and the acquired image data sets are utilized to produce a posterior distribution, such as a posterior distribution of image gradients. From this posterior distribution, multiple images with the different contrast characteristics are reconstructed. The medical imaging system may be a magnetic resonance imaging system, an x-ray computed tomography imaging system, an ultrasound system, and so on.

24 Claims, 3 Drawing Sheets

(51) Int. Cl.
*G01R 33/48* (2006.01)
*G01R 33/56* (2006.01)
*G01R 33/563* (2006.01)

(56) References Cited

U.S. PATENT DOCUMENTS

| | | | |
|---|---|---|---|
| 2008/0146914 A1* | 6/2008 | Polzin et al. | 600/420 |
| 2009/0147919 A1* | 6/2009 | Goto et al. | 378/86 |
| 2009/0161932 A1* | 6/2009 | Chen | G06T 11/006 382/131 |
| 2009/0161933 A1* | 6/2009 | Chen | 382/131 |
| 2010/0011268 A1* | 1/2010 | Sinop et al. | 714/746 |
| 2010/0014730 A1 | 1/2010 | Hahn et al. | |
| 2010/0194392 A1 | 8/2010 | Torheim et al. | |
| 2010/0296717 A1* | 11/2010 | Takizawa | G01R 33/4824 382/131 |

OTHER PUBLICATIONS

Ji et al, "Multitask Compressive Sensing", IEEE Transactions on Signal Processing, vol. 57, No. 1, Jan. 2009.*
Petrovic, Gradient-Based Multiresolution Image Fusion, Feb. 2004, IEEE Transactions on Image Processing, vol. 13, No. 2, pp. 228-237.*
The International Search Report and Written Opinion as mailed on Jan. 27, 2012 for International Application No. PCT/US2011/051309.
Lustig et al., "Compressed Sensing MRI", Jul. 2007; Technical Reports No. 2007-3; Dept. of Statistics, Stanford University.

* cited by examiner

MULTI-CONTRAST IMAGE RECONSTRUCTION WITH JOINT BAYESIAN COMPRESSED SENSING

CROSS-REFERENCE TO RELATED APPLICATIONS

This application represents the national stage entry of PCT International Application No. PCT/US2011/051309 filed on Sep. 13, 2011, and claims the benefit of U.S. provisional patent application No. 61/382,563, filed on Sep. 14, 2010. The disclosure of each of these applications is hereby incorporated by reference as if set forth in their entirety herein.

STATEMENT REGARDING FEDERALLY SPONSORED RESEARCH

This invention was made with government support under EB007942 Awarded by the National Institutes of Health. The government has certain rights in the Invention.

BACKGROUND OF THE INVENTION

The field of the invention is systems and methods for medical imaging. More particularly, the invention relates to systems and methods for medical image reconstruction.

Magnetic resonance imaging ("MRI") uses the nuclear magnetic resonance ("NMR") phenomenon to produce images. When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped," into the x-y plane to produce a net transverse magnetic moment $M_{xy}$. A signal is emitted by the excited nuclei or "spins," after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically-proven pulse sequences and they also enable the development of new pulse sequences.

In clinical applications of MRI, it is often beneficial to image the same region of interest under multiple contrast settings because this makes it possible to emphasize different tissue types. The fact that different pathologies exhibit different relaxation times makes multi-contrast scans very valuable for diagnostics.

Recently, a new mathematical framework for image reconstruction termed "compressed sensing" ("CS") was formulated. According to compressed sensing theory, only a small set of linear projections of a compressible image are required to reconstruct an accurate image. The theory of CS is described, for example, by E. Candès, et al., in "Robust Uncertainty Principles: Exact Signal Reconstruction from Highly Incomplete Frequency Information," *IEEE Transactions on Information Theory*, 2006; 52:489-509; and by D. Donoho in "Compressed Sensing," *IEEE Transactions on Information Theory*, 2006; 52:1289-1306; and is disclosed, for example, in U.S. Pat. No. 7,646,924. Given a set of underdetermined linear equations:

$$y = \phi x \qquad (1);$$

where $x \in \mathbb{R}^M$, $y \in \mathbb{R}^K$, and $\Phi \in \mathbb{R}^{K \times M}$ with K<M, compressed sensing theory aims to find the sparsest solution in an orthonormal basis, $\Psi$, by solving the following constrained optimization problem:

$$\hat{x} = \underset{x}{\operatorname{argmin}} \|\Psi^T x\|_1 \text{ such that } y = \Phi x. \qquad (2)$$

Magnetic resonance imaging is one of the areas where compressed sensing has received abundant attention. This is because the data collected during an MRI scan are in Fourier space, or "k-space"; therefore, reconstructing images from this data involves solving an inverse problem. Because the duration of an MRI scan is related to the number of data points that are sampled in k-space, it is of interest to obtain compressive samples and speed up data acquisition. Making use of CS theory to this end was first proposed by M. Lustig, et al., in "Sparse MRI: The Application of Compressed Sensing for Rapid MR Imaging," *Magn. Reson. Med.*, 2007; 58(6): 1182-95, in which the inversion problem was formulized as:

$$\hat{x} = \underset{x}{\operatorname{argmin}} \|\Psi^T x\|_1 + \beta \cdot TV(x) \text{ such that } \|y - F_\Omega x\|_2 < \varepsilon; \qquad (3)$$

where y is allowed to be complex valued, $\Psi$ is a wavelet basis, TV ( . . . ) indicates the total variation operation, $\beta$ is a parameter that trades wavelet sparsity with finite differences sparsity, $F_\Omega$ is an undersampled Fourier transform operator containing only the frequencies $\omega \in \Omega$, and $\varepsilon$ is a threshold parameter that is tuned for each reconstruction task.

In light of the foregoing, it would be desirable to provide an image reconstruction method that can produce accurate images from few data samples, such as compressed sensing, but can do so while simultaneously reconstructing multiple images from a plurality of different data sets acquired with different contrast characteristics. Currently available image reconstruction methods that employ compressed sensing do not utilize information sharing among multiple image data sets acquired with differing contrast or other imaging characteristics.

SUMMARY OF THE INVENTION

The present invention overcomes the aforementioned drawbacks by providing a system and method for reconstructing multiple images with different contrast characteristics from a related plurality of image data sets. The plurality of image data sets are acquired with one or more medical imaging systems and the image data sets are used to estimate hyperparameters that characterize a prior distribution on image gradient coefficients, or coefficients in another domain. These hyperparameters and the acquired data are then utilized to produce a posterior estimate for the image gradients or other domain parameters. Based on this estimate, multiple images with the different contrast characteristics are reconstructed.

It is an aspect of the invention to provide a method for reconstructing images of a subject with a magnetic resonance imaging ("MRI") system. Multiple image data sets with different contrast characteristics are acquired with the MRI system. In some instances, at least one of the multiple image data sets may be fully sampled, from which a prior image can be reconstructed. Hyperparameters related to a prior distribution are estimated from the multiple image data sets. If a prior image is reconstructed, it may be used to initialize the estimation of the hyperparameters. For example, the prior image may be used to initialize an expectation-maximization algorithm used to estimate the hyperparameters. A posterior distribution is then produced using the estimated hyperparameters, and multiple images of the subject are produced using the posterior distribution and the multiple image data sets. Each of these produced multiple images have an image contrast associated with a contrast characteristic of the respective one of the multiple image data sets.

It is another aspect of the invention to provide a method for reconstructing images of a subject from medical image data acquired with a medical imaging system. At least two medical image data sets are acquired with at least one medical imaging system, in which each of the at least two medical image data sets are acquired with a selected contrast characteristic. Hyperparameters related to a prior distribution of image gradient coefficients are estimated from the at least two medical image data sets, and a posterior distribution of image gradients is produced using the estimated hyperparameters and the at least two medical image data sets. Using the produced posterior distribution of image gradients, images of the subject are reconstructed. Hyperparameters may be estimated using a maximum-likelihood algorithm and an expectation-maximization algorithm. With the latter, a fully sampled image data set may be acquired, from which a prior image can be reconstructed and used to initialize the expectation-maximization algorithm.

It is another aspect of the invention that the medical imaging system may be a magnetic resonance imaging ("MRI) system, an x-ray computed tomography ("CT") imaging system, an ultrasound system, a positron emission tomography ("PET") system, a single photon emission computed tomography ("SPECT") system, an optical imaging system, an electroencephalography ("EEG") system, and a magnetoencephalography ("MEG") system.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

A probabilistic framework that makes use of the similarities between the images with different contrast characteristics in order to reconstruct images from undersampled data is provided. Compared to conventional compressed sensing ("CS") algorithms that work on each of the images independently, the provided joint inversion technique improves the achievable quality of images reconstructed as compared to those reconstructed at the same undersampling ratio with other CS methods. Additionally, similar quality results are obtained at higher undersampling ratios with less data. Moreover, the presented image reconstruction method can also make use of different imaging characteristics between images. For example, some imaging sequences may be used to acquire images with certain contrast characteristics relatively faster than others. Thus, in some instances, it may be advantageous to acquire a fully sampled image as prior information to help reconstruct images from undersampled image data. As a result, it is possible in these instances to use a fully-sampled fast imaging sequence to help reconstruct images from undersampled image data acquired with slower imaging sequences.

In general, all CS algorithms exploit the prior knowledge that the signal of interest can be approximated to be sparse in some transform domain. Bayesian compressed sensing is a principled way of achieving this, wherein a sparsity promoting prior is defined over the transform coefficients and the aim is to find a posterior distribution of these coefficients given related measurements. In the multi-contrast MRI setting with L different scans, the vertical and horizontal image gradients, $\{\delta_i^x\}_{i=1}^L$ and $\{\delta_i^y\}_{i=1}^L$, respectively, that belong to the unknown signals, $\{x_i\}_{i=1}^L$, are estimated. In some instances, L+1 different scans may be performed, in which L of such scans are performed with undersampling in k-space, and one of them is performed such that a fully sampled image, $x_{prior}$, is obtained.

The image gradients are selected because they are quite sparse in agreement with CS theory, which requires a sparse signal to enable reconstruction from undersampled measurements. Moreover, while the image gradients are quite sparse, the actual images they represent are typically not as sparse as desirable. Thus, the image gradients serve as a sparse representation of the desired images. By reconstructing the image gradients in accordance with the herein described method, the images that are consistent with these gradients can be determined. It will be appreciated by those skilled in the art that sparse domains other than the image gradient domain can similarly be utilized in lieu of the image gradient domain. These unknown signals, $\{x_i\}_{i=1}^L$, are sensed via the measurements:

$$y_i = F_\Omega x_i \text{ for } \{y_i\}_{i=1}^L \in \mathbb{C}^M \qquad (4).$$

The k-space measurements belonging to the image gradients can be obtained by modifying the measurement, $y_i$, as follows:

$$F_\Omega \delta_i^x(\omega, \nu) = (1 - e^{-2\pi j \omega/n}) y_i(\omega, \nu) \equiv y_i^x \qquad (5);$$

$$F_\Omega \delta_i^y(\omega, \nu) = (1 - e^{-2\pi j \nu/m}) y_i(\omega, \nu) \equiv y_i^y \qquad (6);$$

where $y_i^x$ and $y_i^y$ are the modified observations; $F_\Omega$ are the undersampled Fourier operators containing only the frequencies $\omega \in \Omega$; and $\omega$ and $\nu$ index the frequency space of an n×m=M image, with $j=\sqrt{-1}$. A further assumption that the modified data are corrupted by circular symmetric complex Gaussian noise with variance $\sigma^2$ can be made. This assumption provides the following observation model for the vertical image gradients:

$$y_i^x = F_\Omega \delta_i^x + n_i \quad (7)$$

for $i=1, \ldots, L$, where $n_i$ is the Gaussian noise for the $i^{th}$ measurement. An observation model for the horizontal image gradients can be similarly expressed as:

$$y_i^y + F_\Omega \delta_i^y + n_i \quad (8)$$

Throughout the following description, reference will be made to expressions related to the vertical image gradient, $\delta_i^x$; however, it will be readily appreciated by those skilled in the art that it is mathematically straightforward to define an analogous expression for the horizontal image gradient, $\delta_i^y$, following from Eqn. (8) in lieu of Eqn. (7).

With the foregoing formulation, the data likelihood for the vertical image gradient can be expressed as:

$$p(y_i^x | \delta_i^x, \sigma^2) = (\pi\sigma^2)^{-M} \exp\left(-\frac{1}{\sigma^2}\|y_i^x - F_\Omega \delta_i^x\|^2\right). \quad (9)$$

In the instances where a fully-sampled image, $x_{prior}$, is acquired, it is straightforward to compute the associated image gradients, $\delta_{prior}^x$ and $\delta_{prior}^y$, as follows:

$$\delta_{prior}^x = F^{-1}\{(1-e^{-2\pi j v/n}) y_{prior}(\omega, v)\} \quad (10)$$

$$\delta_{prior}^y = F^{-1}\{(1-e^{-2\pi j v/m}) y_{prior}(\omega, v)\} \quad (11)$$

where F is the fully sampled Fourier operator and $y_{prior}$ is the fully sampled image data set, from which the prior image, $x_{prior}$, is reconstructed. As will be described below in detail, the image gradients associated with the prior image can be used to initialize the estimation of hyperparameters for use in a Bayesian compressed sensing reconstruction.

In addition to the Gaussian likelihood model provided in Eqn. (9), joint Bayesian compressed sensing places hyperparameters across each pixel of the multi-contrast images to couple them. Sparsity enforcing priors may be introduced via a hierarchical Bayesian model, which also provides for information sharing across the CS inversion tasks. Hierarchical Bayesian representations provide the ability to capture both the individuality of the inversion tasks and the relations between them. This characteristic is illustrated in the graphical model shown in FIG. 1. At the bottom layer 102 are the linear observations, $y_i$, provided by Eqns. (7) and (8), which are jointly parameterized by the priors $\alpha \in \mathbb{R}^M$ and $\alpha_0 = \sigma^{-2}$ on the layer above 104. These priors, $\alpha \in \mathbb{R}^M$ and $\alpha_0 = \sigma^{-2}$, are, in turn, controlled by the hyperpriors, a, b, c, and d, at the top level 106 of the hierarchy.

Figure 1:
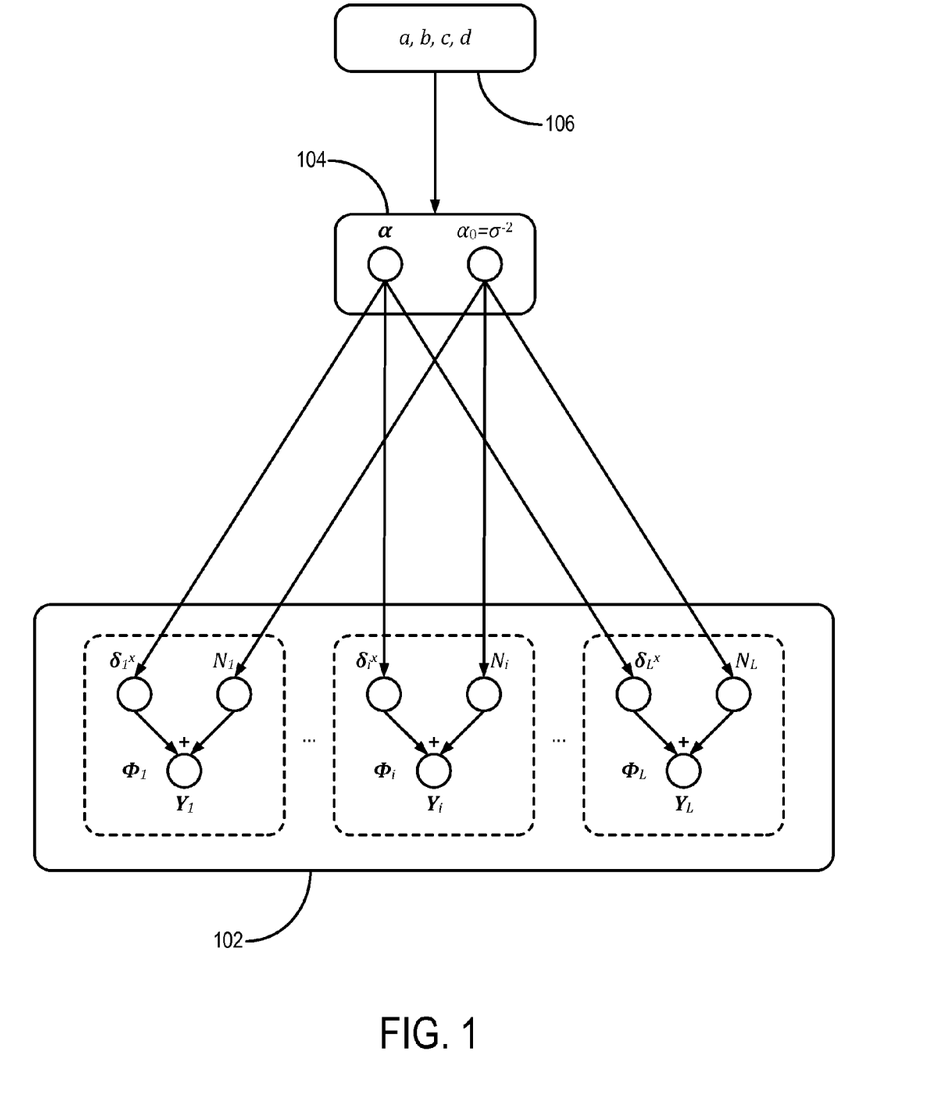
FIG. 1 is a graphic representation of a Bayesian network depicting a hierarchical model related to a multi-contrast inference problem, in which a series of individual linear observations are connected to each other via common priors on the layer above, which are in turn adjusted by the hyperpriors at the top level.

According to this model, the image gradient coefficients are assumed to be drawn from a product of zero mean normal distributions with precisions determined by the hyperparameters, $\alpha$.

$$p(\delta_j | \alpha_j) = \mathcal{N}(0, \alpha_j I) \quad (12)$$

where $\delta_j$ represents the L-dimensional vector formed by taking the $j^{th}$ pixel in each multi-contrast image, and $\mathcal{N}(0, \alpha_j I)$ is an L-dimensional zero mean Gaussian distribution with variance $\alpha_j$, and in which I is an identity matrix. By multiplicative combination of all such pixels, a full prior distribution may be formed, as follows:

$$p(\delta | a) = \prod_{j=1}^{N} \mathcal{N}(0, \alpha_j I); \quad (13)$$

where $\alpha = [\alpha_1, \ldots, \alpha_N]^T$ is a vector of hyperparameters, and $\delta = [\delta_1, \ldots, \delta_L]$ is a matrix formed by the gradients of the L images. Combining this prior and the Gaussian likelihood with Bayes' rule yields the posterior distribution for the $i^{th}$ image gradient:

$$p(\delta_i^x | y_i^x, \alpha) = \mathcal{N}(\mu_i, \Sigma) \quad (14);$$

where the mean and covariance of the posterior distribution are given as:

$$\mu_i = A F_\Omega^H \Sigma_t^{-1} y_i^x \quad (15)$$

and $$\Sigma = A - A F_\Omega^H \Sigma_t^{-1} F_\Omega A \quad (16);$$

respectively. In Eqns. (15) and (16), the superscript $(\ldots)^H$ denotes the Hermitian operation, $A = \text{diag}(\alpha)$, and, $$\Sigma_t^{-1} = (\sigma^2 I + F_\Omega A F_\Omega^H)^{-1} \quad (17).$$

Because the posterior distribution for the gradient coefficients is fully characterized if the hyperparameter vector is known, these parameters are estimated, as will be described below in detail.

Because the hyperparameters, $\alpha$, are shared among the L, or L+1, CS tasks, data from all observations contribute to their estimation. This offers the possibility of borrowing strength across the inversion problems, which is beneficial for reconstructing the multi-contrast images.

In order to promote sparsity in the gradient domain, Gamma priors may be defined over the hyperparameters, $\alpha$, and the noise precision, $\alpha_0$, as:

$$p(\alpha_0 | a, b) = Ga(\alpha_0 | a, b) = \frac{b^a}{\Gamma(a)} \alpha_0^{a-1} e^{-b\alpha_0}; \quad (18)$$

$$p(\alpha | c, d) = \prod_{j=1}^{M} Ga(\alpha_j | c, d). \quad (19)$$

Here, the hyperparameters, $\alpha$, and noise precision, $\alpha_0$, are modeled to be drawn from Gamma distributions parameterized by the hyperpriors a, b, c, and d. The task is then to find the hyperparameters that make the observed data most likely. Thus, the hyperpriors reflect the prior belief about the values of the hyperparameters before seeing the observed data. Using this information, a posterior belief is formed with a maximum likelihood approach after obtaining the data, as will be described below in detail. To demonstrate how the Gamma prior encourages sparsity on the signal coefficients, the hyperparameters can be integrated out to obtain the marginal prior:

$$p(\delta_{i,j}^x) = \int p(\delta_{i,j}^x | \alpha_j) p(\alpha_j | c, d) d\alpha_j \quad (20).$$

Eqn. (19) corresponds to a Student's t-density function over the $j^{th}$ coefficient, so the marginal prior is a multiplication of independent Student's t-distributions. In the particular case of uniform hyperpriors, with $c=d=0$, improper priors of the form:

$$p(\delta_{i,j}^x) \propto \frac{1}{|\delta_{i,j}^x|}; \quad (21)$$

are obtained. This favors sparse entries due to the sharp peak at zero.

Given the L acquired data sets, $\{y_i\}_{i=1}^L$ it is possible to infer a posterior distribution on the hyperparameters $\alpha$ and $\alpha_0$. However, this inference includes M-dimensional integrals over the hyperparameters and the gradient coefficients. Therefore, it is often times more practical to seek point estimates for the hyperparameters in a maximum likelihood ("ML") framework. These point estimates are determined by searching for the hyperparameter setting that makes the observation of the k-space data most likely. Such an optimization process is referred to as an evidence maximization, or type-II maximum likelihood, method.

For example, the point estimates for $\alpha$ and $\alpha_0$ may be obtained by maximizing the log likelihood:

$$\mathcal{L}(a, \alpha_0) = \sum_{i=1}^L \log p(Y_i \mid a, \alpha_0) \quad (22)$$

$$= -\frac{1}{2} \sum_{i=1}^L 2K_i \log(2\pi) + \log|C_i| + Y_i^T C_i^{-1} Y_i;$$

with $$C_i = \alpha_0^{-1} I + \Phi_i A^{-1} \Phi_i^T; \quad (23)$$

where I is the identity matrix. For simplicity, the following notation may be used:

$$Y_i^x = \Phi_i \delta_i^x + N_i \quad (24);$$

and $$Y_i^y = \Phi_i \delta_i^y + N_i \quad (25);$$

where $Y_i^x, Y_i^y, N_i \in \mathbb{R}^{2K_i}$, and $\Phi_i \in \mathbb{R}^{2K_i \times M}$ correspond to the respective concatenated variables in the following respective observation models:

$$\begin{bmatrix} \Re(y_i^x) \\ \Im(y_i^x) \end{bmatrix} = \begin{bmatrix} \Re(F_{\Omega_i}) \\ \Im(F_{\Omega_i}) \end{bmatrix} \delta_i^x + \begin{bmatrix} \Re(n_i) \\ \Im(n_i) \end{bmatrix}; \quad (26)$$

and $$\begin{bmatrix} \Re(y_i^y) \\ \Im(y_i^y) \end{bmatrix} = \begin{bmatrix} \Re(F_{\Omega_i}) \\ \Im(F_{\Omega_i}) \end{bmatrix} \delta_i^y + \begin{bmatrix} \Re(n_i) \\ \Im(n_i) \end{bmatrix}. \quad (27)$$

for $i=1, \ldots, L$, where $\Re(\ldots)$ indicates the real part; $\Im(\ldots)$ indicates the imaginary part; and $n_i$ is the Gaussian noise for the $i^{th}$ measurement.

It is noted that data from all L measurements contribute to the evidence maximization procedure via the summation over conditional distributions. Hence, the information sharing across the images occurs through this collaboration in the maximum likelihood estimation of the hyperparameters. Once the point estimates are constituted using all of the observations, the posterior for the signal coefficients, $\delta_i^x$, is estimated based on its related k-space data, $Y_i$. Thus, all of the measurements are used in the estimation of the hyperparameters, but only the associated data are utilized to constitute an approximation to the gradient coefficients.

Once the ML estimates for the hyperparameters are obtained, the posterior distribution over the sparse coefficients can be analytically evaluated by invoking Bayes' Theorem:

$$p(\delta_i^x \mid Y_i, \alpha, \alpha_0) = \frac{p(Y_i \mid \delta_i^x, \alpha) p(\delta_i^x \mid \alpha_0)}{p(Y_i \mid \alpha, \alpha_0)} = \mathcal{N}(\delta_i^x \mid \mu_i, \Sigma_i); \quad (28)$$

with mean and covariance respectively given by:

$$\mu_i = \alpha_0 \Sigma_i \Phi_i^T Y_i \quad (29);$$

$$\Sigma_i = (\alpha_0 \Phi_i^T \Phi_i + A)^{-1} \quad (30);$$

where $A = \text{diag}(\alpha_1, \ldots, \alpha_M)$ is a diagonal matrix populated with the entries in $\alpha$.

Differentiating Eqn. (30) with respect to $\alpha$ and $\alpha_0$, and setting the result to zero gives the following update rules:

$$\alpha_j^{new} = \frac{L - \alpha_j \sum_{i=1}^L \Sigma_{i,(j,j)}}{\sum_{i=1}^L \mu_{i,j}^2}, \quad j \in \{1, \ldots, M\}; \quad (31)$$

$$\alpha_0^{new} = \frac{\sum_{i=1}^L \left( 2K_i - M + \sum_{j=1}^M \alpha_j \Sigma_{i,(j,j)} \right)}{\sum_{i=1}^L \|Y_i - \Phi_i \mu_i\|_2^2}; \quad (32)$$

where $\Sigma_{i,(j,j)}$ is the $j^{th}$ diagonal entry of the covariance matrix, $\Sigma_i$. Because the updates for the hyperparameters, $\alpha^{new}$ and $\alpha_0^{new}$, depend on $\{\mu_i\}_{i=1}^L$ and $\{\Sigma_i\}_{i=1}^L$, which are in turn functions of the hyperparameters, it is possible to estimate all four variables via an EM-like iterative scheme that alternates between Eqns. (29)-(30) and Eqns. (31)-(32). Even though this might be feasible for small scale problems, the task becomes computationally difficult because it requires inverting an M×M matrix while evaluating Eqn. (30). However, with the appropriate treatment, such an approach is feasible without undue computational burden, as will be described below in detail. The next section presents an alternative approach to overcome this problem, and removes the algorithm's dependence on the noise precision estimate, $\alpha_0$.

Even though the estimate for the noise variance is updated in the ML iterations, an initial guess for $\alpha_0$ is still required. Apart from the fact that an inappropriate guess may degrade the algorithm's performance, it will be necessary to tune this data-dependent parameter each time a different data set is being reconstructed. To alleviate this dependency, this parameter can be integrated out rather than seeking a point estimate for it. This is achieved by modifying the prior on the coefficients as:

$$p(\delta_i^x \mid \alpha, \alpha_0) = \prod_{j=1}^M \mathcal{N}(\delta_{i,j}^x \mid 0, \alpha_j^{-1} \alpha_0^{-1}); \quad (33)$$

where again a Gamma prior is defined over $\alpha_0$ as $p(\alpha_0 \mid a, b) = \text{Ga}(\alpha_0 \mid a, b)$. It is possible to analytically integrate out $\alpha_0$ in the posterior for the image gradient, $\delta_i^x$, with the following formulation:

$$p(\delta_i^x \mid Y_i, \alpha) = \int p(\delta_i^x \mid Y_i, \alpha, \alpha_0) p(\alpha_0 \mid a, b) d\alpha \quad (34)$$

$$= \frac{\Gamma\left(a + \frac{M}{2}\right)}{\Gamma(a)(2\pi b)^{M/2} |\Sigma_i|^{1/2}};$$

$$\left(1 + \frac{1}{2b}(\delta_i^x - \mu_i)^T \Sigma_i^{-1}(\delta_i^x - \mu_i)\right)^{a+M/2}$$

with $$\mu_i = \Sigma_i \Phi_i^T Y_i; \quad (35)$$

$$\Sigma_i = (\Phi_i^T \Phi_i + A)^{-1}. \quad (36)$$

The posterior on the sparse coefficients has now become a multivariate Student's t-distribution, which is more resilient in allowing outlying measurements. Now that we added robustness to the algorithm and got rid of a parameter that needs to be tuned, we seek a workaround to the sometimes impractical matrix inversion in Eqn. (30). Again starting with the type-II maximum likelihood expression for the hyperparameters, $\alpha$:

$$\mathcal{L}(\alpha) = \sum_{i=1}^{L} \log p(Y_i \mid \alpha) \quad (37)$$

$$= \sum_{i=1}^{L} \int p(\alpha_0 \mid a, b) p(\delta_i^x \mid \alpha, \alpha_0) p(Y_i \mid \delta_i^x, \alpha_0) d\delta_i^x d\alpha_0$$

$$= -\frac{1}{2} \sum_{i=1}^{L} (2K_i + 2a) \log(Y_i^T B_i^{-1} Y_i + 2b) + \log|B_i| + C;$$

where C is a constant and:

$$B_i = I + \Phi_i A^{-1} \Phi_i^T \quad (38).$$

It is possible to decompose the matrix $B_i$ by considering its dependence on a single hyperparameter, $\alpha_j$, $j \in \{1, \ldots, M\}$, as follows:

$$B_i = I + \Phi_i A^{-1} \Phi_i^T \quad (39)$$

$$= I + \sum_{k \neq j} \alpha_k^{-1} \Phi_{i,k} \Phi_{i,k}^T + \alpha_j^{-1} \Phi_{i,j} \Phi_{i,j}^T$$

$$= B_{i,-j} + \alpha_j^{-1} \Phi_{i,j} \Phi_{i,j}^T.$$

Here, $B_{i,-j}$ is $B_i$ with the contribution of the $j^{th}$ basis function, $\Phi_{i,j}$, removed. In order to decompose $\mathcal{L}(\alpha)$ similarly, the Woodbury matrix identity and the matrix determinant lemma are employed:

$$B_i^{-1} = B_{i,-j}^{-1} + \frac{B_{i,-j}^{-1} \Phi_{i,j} \Phi_{i,j}^T B_{i,-j}^{-1}}{\alpha_j + \Phi_{i,j}^T B_{i,-j}^{-1} \Phi_{i,j}}; \quad (40)$$

$$|B_i| = |B_{i,-j}| |1 + \alpha_j^{-1} \Phi_{i,j}^T B_{i,-j}^{-1} \Phi_{i,j}|. \quad (41)$$

Applying Eqns. (40) and (41) to Eqn. (37) yields:

$$\mathcal{L}(\alpha) = -\frac{1}{2} \sum_{i=1}^{L} (2K_i + 2a) \log\left(\frac{1}{2} Y_i^T B_{i,-j}^{-1} Y_i + b\right) + \log|B_{i,-j}| + C \quad (42)$$

$$= -\frac{1}{2} \sum_{i=1}^{L} \log(1 + \alpha_j^{-1} s_{i,j}) + (2K_i + 2a) \log\left(1 - \frac{q_{i,j}^2 / g_{i,j}}{\alpha_j + s_{i,j}}\right)$$

$$= \mathcal{L}(\alpha_{-j}) + l(\alpha_j).$$

Here $l(\alpha_j)$ is the component of the log likelihood that depends only on the $j^{th}$ hyperparameter, and $\mathcal{L}(\alpha_{-j})$ represents the part of the log likelihood dependent on all the remaining hyperparameters in $\alpha$. The auxiliary variables are defined as:

$$s_{i,j} \triangleq \Phi_{i,j}^T B_{i,-j}^{-1} \Phi_{i,j} \quad (43);$$

$$q_{i,j} \triangleq \Phi_{i,j}^T B_{i,-j}^{-1} Y_i \quad (44);$$

$$g_{i,j} \triangleq Y_i^T B_{i,-j}^{-1} Y_i + 2b \quad (45).$$

To find the value of $\alpha_j$ that maximizes the log likelihood, Eqn. (42) is differentiated with respect to $\alpha_j$ and the result set to zero. This leads one to the optimal solution:

$$\alpha_j = \frac{L}{\sum_{i=1}^{L} \frac{(2K_i + 2a) q_{i,j}^2 / g_{i,j}^2 - s_{i,j}}{s_{i,j}(s_{i,j} - q_{i,j}^2 / g_{i,j})}}; \quad (46)$$

if $\sum_{i=1}^{L} \frac{(2K_i + 2a) q_{i,j}^2 / g_{i,j}^2 - s_{i,j}}{s_{i,j}(s_{i,j} - q_{i,j}^2 / g_{i,j})} > 0$, otherwise, $\alpha_j = \infty$;

Since setting $\alpha_j = \infty$ corresponds to shrinking $\delta_{i,j}^x$ to zero, the basis functions, for $\Phi_{i,j}$ for $i \in \{1, \ldots, L\}$ will have no effect in representing the sparse approximations. This suggests a sequential algorithm, in which we begin with a single basis vector for each signal, then keep adding the basis function that yields the largest increase in the log likelihood at each iteration. Alternatively, a hyperparameter corresponding to a basis vector that is already in the dictionary of current bases can be updated or deleted, if this gives rise to the largest increase in the likelihood at that iteration.

Another refinement in the joint Bayesian CS algorithm is to replace the observation matrices, $\{\Phi_i\}_{i=1}^{L}$, with the fast Fourier transform ("FFT"). This provides the ability to work with MR images of practical sizes; otherwise, each of the observation matrices may occupy up to two gigabytes ("GB") of memory, even for a 128×128 image matrix.

Another approach for estimating the hyperparameters, $\alpha$, using an expectation-maximization ("EM") algorithm is now described. In Bayesian compressed sensing, evidence maximization may be used to integrate out the image gradient coefficients from the likelihood model. In this manner, the marginal likelihood that depends on the k-space data is then maximized with respect to the hyperparameters. In other words, the hyperparameter vector, $\alpha$, that explains the acquired k-space data the best is taken to be the optimal hyperparameter setting.

With an EM algorithm the first step, the expectation step or "E-step," is to estimate the missing data using the observed data and current estimates of the model parameters. Here, this is done using Eqns. (15) and (16). The second step, the maximization step or "M-step," is to maximize the likelihood function under the assumption that the missing data are known. This latter step is performed as follows:

$$\alpha_j^{new} = \frac{\|\mu_j\|^2}{L - L\alpha_j^{-1}\Sigma_{jj}} \text{ for } j=1,\ldots,N; \qquad (47)$$

where $\Sigma_{jj}$ is the $j^{th}$ diagonal entry in $\Sigma$, and $\mu_j$ is the L-dimensional vector formed by the $j^{th}$ pixel in the image gradients. The practical consideration with the approach, as noted above, is that the computation of $\Sigma$ includes the inversion of the matrix in Eqn. (17), which is an M×M sized matrix that can easily exceed $10^8$ matrix entries in clinical MRI. Thus, convention matrix inversion techniques are not applicable for such a large scale problem. To address this setback, an approximate eigendecomposition method, such as the Lanczos algorithm with partial reorthogonalization, is utilized in the inversion of the matrix in Eqn. (17). Using the Lanczos algorithm the inversion can be approximated as:

$$\Sigma_t^{-1} \approx QT^{-1}Q^H \qquad (48);$$

where $Q \in \mathbb{C}^{M \times K}$ is orthonormal, and $T \in \mathbb{C}^{K \times K}$ is a tridiagonal matrix, which can be rapidly inverted. Here, K is the number of eigenvectors in the decomposition, and the quality of inversion increases as K approaches M. In practice, the Lanczos algorithm is memory efficient because the only storage requirement comes from the Q matrix, and there is no need to form the actual $\Sigma_t^{-1}$ matrix because implementing it as a matrix-vector product using a fast Fourier transform is sufficient.

Running the EM iterations for the fully-sampled, known image gradient, $\delta_{prior}^x$, results in the following:

$$\Sigma_{prior} = 0 \qquad (49);$$

$$\mu_{prior} = \delta_{prior}^x \qquad (50);$$

and $$\alpha_j^{prior} = |\mu_{prior,j}|^2 \qquad (51).$$

The EM iterations do not alter the known signal, $\delta_{prior}^x$, and they derive hyperparameters from the prior image, $\alpha_{prior} = [|\delta_{prior,1}^x|^2, \ldots, |\delta_{prior,N}^x|^2]^T$ that is used to initialize the hyperparameters in the EM iterations for the undersampled images. This way, the known sparsity support of the prior image facilitates the reconstruction of the undersampled images.

Once the image gradients, $\{\delta_i^x\}_{i=1}^L$ and $\{\delta_i^y\}_{i=1}^L$, are estimated with the joint Bayesian algorithm, the images, $\{x_i\}_{i=1}^L$, consistent with these gradients and the undersampled measurements, $\{Y_i\}_{i=1}^L$, are sought. This is formulated as a least squares ("LS") optimization problem of the following form:

$$\hat{x}_i = \underset{x_i}{\operatorname{argmin}} \|\partial_x x_i - \delta_i^x\|_2^2 + \|\partial_y x_i - \delta_i^y\|_2^2 + \lambda\|F_{\Omega_i} x_i - Y_i\|_2^2; \qquad (52)$$

for $i = 1, \ldots, L$, where $\partial_x x_i$ and $\partial_y x_i$ represent vertical and horizontal image gradients, respectively. Using Eqns. (5) and (6), and invoking Parseval's Theorem, the optimization problem can be cast into k-space as:

$$\hat{X}_i = \underset{X_i}{\operatorname{argmin}} \|(1 - e^{-2\pi j\omega/n})X_i - \Delta_i^x\|_2^2 + \qquad (53)$$
$$\|(1 - e^{-2\pi jv/m})X_i - \Delta_i^y\|_2^2 + \lambda\|X_{\Omega_i} - Y_i\|_2^2;$$

where $X_i$, $\Delta_i^x$, and $\Delta_i^y$ are Fourier transforms of $x_i$, $\delta_i^x$, and $\delta_i^y$, respectively; and $X_{\Omega_i}$ is the transform of $x_i$ restricted to the frequency set $\Omega_i$. Based on this, a solution is arrived at by representing Eqn. (53) as a quadratic polynomial and finding the root with $\lambda \to \infty$. Such a solution is given by:

$$\hat{X}_i(\omega, v) = \begin{cases} X_{\Omega_i} & \text{if } (\omega, v) \in \Omega_i \\ \frac{(1 - e^{-2\pi j\omega/n})\Delta_i^x + (1 - e^{-2\pi jv/m})\Delta_i^y}{|1 - e^{-2\pi j\omega/n}|^2 + |1 - e^{-2\pi jv/m}|^2} & \text{otherwise} \end{cases} \qquad (54)$$

Taking the inverse Fourier transform of the solution calculated with Eqn. (54) yields the reconstructed images, $\{\hat{x}_i\}_{i=1}^L$.

Figure 2:
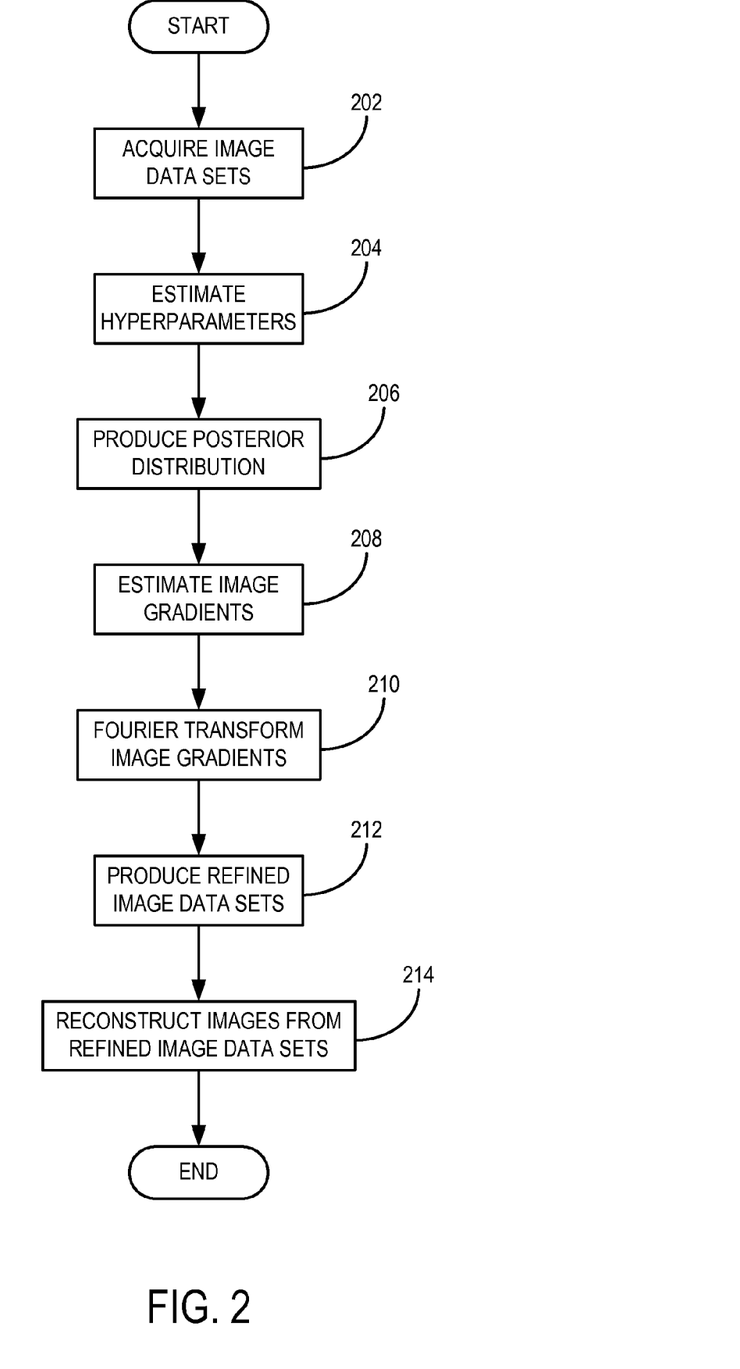
FIG. 2 is a flowchart setting forth the steps of an example of a joint Bayesian compressed sensing image reconstruction method.

Referring particularly now to FIG. 2, a flowchart setting forth the steps of an example of a joint Bayesian compressed sensing image reconstruction method in accordance with the present invention is illustrated. The method begins with the acquisition of L different image data sets from a subject using one or more medical imaging systems, as indicated at step 202. In the alternative, L+1 different image data sets may be acquired, in which L of the image data sets are undersampled and one of the image data sets is fully sampled. For example, a magnetic resonance imaging ("MRI") system can be employed to acquire L different image data sets, each having a different contrast characteristics such as a $T_1$-weighting, a $T_2$-weighting, a $T^*_2$-weighting, a $T_{1\rho}$-weighting, a proton density weighting, a diffusion weighting, and so on. Similarly, an x-ray computed tomography ("CT") system can be employed to acquire L different image data sets, each having a different contrast characteristic such as an x-ray energy level and an x-ray tube current. It should be appreciated by those skilled in the art that other medical imaging systems can similarly be utilized, such as ultrasound systems, positron emission tomography ("PET") systems, single photon emission computed tomography ("SPECT") systems, optical imaging systems, and so on. Moreover, it should be appreciated by those skilled in the art that the L different image data sets acquired with such medical imaging systems can be acquired with different contrast characteristics appropriate to the different medical imaging systems. Similarly, it should be appreciated by those skilled in the art that the L different data sets may also include those acquired with some combination of the aforementioned imaging modalities.

After the desired L, or L+1, image data sets have been acquired, they are utilized to estimate a set of hyperparameters, $\alpha$, that are related to an appropriate prior distribution, as indicated at step 204. In one instance, this estimation may include finding the hyperparameters, $\alpha$, that maximize the log likelihood in Eqn. (42), such as those provided by Eqn. (46). In another instance, this estimation may include employing an expectation-maximization algorithm, as described above, to find the hyperparameters. As noted above, when utilizing an EM algorithm to estimate the hyperparameters, it may be advantageous to initialize the algorithm using the parameters set forth in Eqns. (49)-(51), which may be derived from a fully sampled, prior image of the subject.

The hyperparameters, $\alpha$, are then used to determine a related posterior distribution, as indicated at step 206. This determination is achieved, for example, using Bayes' theorem as applied in Eqns. (28)-(30), Eqns. (34)-(36), or in Eqns. (14)-(16). From the produced posterior distribution, vertical and horizontal image gradients are derived, as indicated at step 208. Utilizing, for example, Eqns. (5) and (6), the vertical and horizontal image gradients are subsequently Fourier transformed, as indicated at step 210. These Fourier transformed image gradients are then utilized to produce a series of refined image data sets that represent the desired L images, as indicated at step 212. These refined image data sets are produced, for example, using the expression in Eqn. (54). From the refined image data sets, the desired multi-contrast images are then reconstructed by Fourier transforming the refined image data sets, as indicated at step 214.

Figure 3:
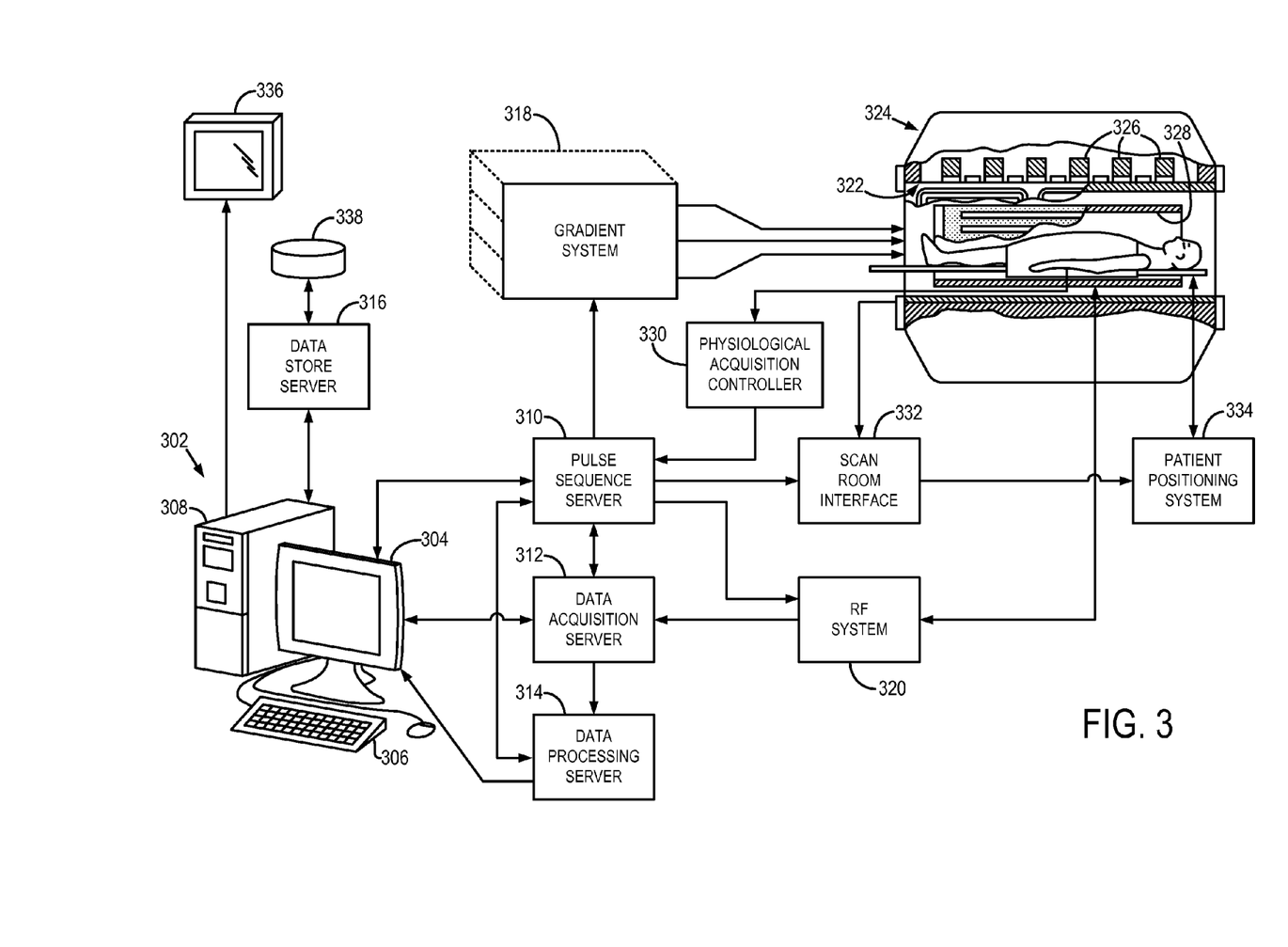
FIG. 3 is a block diagram of an example of a magnetic resonance imaging ("MRI") system.

Referring particularly to FIG. 3, the an embodiment of the invention is employed in a magnetic resonance imaging ("MRI") system 300. The MRI system 300 includes a workstation 302 having a display 304 and a keyboard 306. The workstation 302 includes a processor 308, such as a commercially available programmable machine running a commercially available operating system. The workstation 302 provides the operator interface that enables scan prescriptions to be entered into the MRI system 300. The workstation 302 is coupled to four servers: a pulse sequence server 310; a data acquisition server 312; a data processing server 314, and a data store server 316. The workstation 302 and each server 310, 312, 314 and 316 are connected to communicate with each other.

The pulse sequence server 310 functions in response to instructions downloaded from the workstation 302 to operate a gradient system 318 and a radiofrequency ("RF") system 320. Gradient waveforms necessary to perform the prescribed scan are produced and applied to the gradient system 318, which excites gradient coils in an assembly 322 to produce the magnetic field gradients $G_x$, $G_y$, and $G_z$ used for position encoding MR signals. The gradient coil assembly 322 forms part of a magnet assembly 324 that includes a polarizing magnet 326 and a whole-body RF coil 328.

RF excitation waveforms are applied to the RF coil 328, or a separate local coil (not shown in FIG. 3), by the RF system 320 to perform the prescribed magnetic resonance pulse sequence. Responsive MR signals detected by the RF coil 328, or a separate local coil (not shown in FIG. 3), are received by the RF system 320, amplified, demodulated, filtered, and digitized under direction of commands produced by the pulse sequence server 310. The RF system 320 includes an RF transmitter for producing a wide variety of RF pulses used in MR pulse sequences. The RF transmitter is responsive to the scan prescription and direction from the pulse sequence server 310 to produce RF pulses of the desired frequency, phase, and pulse amplitude waveform. The generated RF pulses may be applied to the whole body RF coil 328 or to one or more local coils or coil arrays (not shown in FIG. 3).

The RF system 320 also includes one or more RF receiver channels. Each RF receiver channel includes an RF amplifier that amplifies the MR signal received by the coil 328 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \qquad \text{Eqn. (55);}$$

and the phase of the received MR signal may also be determined:

$$\phi = \tan^{-1}\left(\frac{Q}{I}\right). \qquad \text{Eqn. (56)}$$

The pulse sequence server 310 also optionally receives patient data from a physiological acquisition controller 330. The controller 330 receives signals from a number of different sensors connected to the patient, such as electrocardiograph ("ECG") signals from electrodes, or respiratory signals from a bellows or other respiratory monitoring device. Such signals are typically used by the pulse sequence server 310 to synchronize, or "gate," the performance of the scan with the subject's heart beat or respiration.

The pulse sequence server 310 also connects to a scan room interface circuit 332 that receives signals from various sensors associated with the condition of the patient and the magnet system. It is also through the scan room interface circuit 332 that a patient positioning system 334 receives commands to move the patient to desired positions during the scan.

The digitized MR signal samples produced by the RF system 320 are received by the data acquisition server 312. The data acquisition server 312 operates in response to instructions downloaded from the workstation 302 to receive the real-time MR data and provide buffer storage, such that no data is lost by data overrun. In some scans, the data acquisition server 312 does little more than pass the acquired MR data to the data processor server 314. However, in scans that require information derived from acquired MR data to control the further performance of the scan, the data acquisition server 312 is programmed to produce such information and convey it to the pulse sequence server 310. For example, during prescans, MR data is acquired and used to calibrate the pulse sequence performed by the pulse sequence server 310. Also, navigator signals may be acquired during a scan and used to adjust the operating parameters of the RF system 320 or the gradient system 318, or to control the view order in which k-space is sampled. The data acquisition server 312 may also be employed to process MR signals used to detect the arrival of contrast agent in a magnetic resonance angiography ("MRA") scan. In all these examples, the data acquisition server 312 acquires MR data and processes it in real-time to produce information that is used to control the scan.

The data processing server 314 receives MR data from the data acquisition server 312 and processes it in accordance with instructions downloaded from the workstation 302. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 314 are conveyed back to the workstation 302 where they are stored. Real-time images are stored in a data base memory cache (not shown in FIG. 3), from which they may be output to operator display 312 or a display 336 that is located near the magnet assembly 324 for use by attending physicians. Batch mode images or selected real time images are stored in a host database on disc storage 338. When such images have been reconstructed and transferred to storage, the data processing server 314 notifies the data store server 316 on the workstation 302. The workstation 302 may be used by an operator to archive the images, produce films, or send the images via a network to other facilities.

The present invention has been described in terms of one or more preferred embodiments, and it should be appreciated that many equivalents, alternatives, variations, and modifications, aside from those expressly stated, are possible and within the scope of the invention. For example, in addition to reconstructing images having different contrast characteristics, images of the same subject from multiple data sets having different imaging characteristics can similarly be reconstructed. Such examples include reconstructing images using spectroscopic MR image data and anatomical MR image data; functional MR image data and anatomical image data; and dynamic image data, including velocity-encoded MR image data and arterial spin-labeled image data, or other temporal image data with a high-resolution structural image data. In addition, it is contemplated that quantitative susceptibility mapping, which normally requires the solution of a poorly conditioned inversion problem from the phase of an MR image, will benefit from the herein described method for joint reconstruction by imposing the problem jointly with a magnitude image.

The invention claimed is:

1. A method for reconstructing images of a subject with a magnetic resonance imaging (MRI) system, the steps of the method comprising:
   a) acquiring with the MRI system, multiple image data sets with different contrast characteristics;
   b) estimating from the multiple image data sets, hyperparameters related to a prior distribution;
   c) producing a posterior distribution of image gradient coefficients using the estimated hyperparameters; and
   d) producing multiple images using the posterior distribution and the multiple image data sets, each of the multiple images having an image contrast associated with a contrast characteristic of the respective one of the multiple image data sets.

2. The method as recited in claim 1 in which step d) includes deriving image gradients from the posterior distribution.

3. The method as recited in claim 2 in which the image gradients are derived in step d) as the mean of the posterior distribution.

4. The method as recited in claim 2 in which step d) includes producing transformed image gradients by performing a Fourier transform on the image gradients.

5. The method as recited in claim 4 in which step d) includes producing multiple refined image data sets using the transformed image gradients.

6. The method as recited in claim 5 in which the multiple images are reconstructed by performing a Fourier transform on the multiple refined image data sets.

7. The method as recited in claim 1 in which step c) includes using Bayes' theorem to produce the posterior distribution using the hyperparameters and the acquired multiple image data sets.

8. The method as recited in claim 1 in which the hyperparameters are estimated in step b) by maximizing a log likelihood.

9. The method as recited in claim 1 in which the prior distribution related to the hyperparameters is a Gamma distribution.

10. The method as recited in claim 1 in which the hyperparameters are estimated in step b) using an expectation-maximization algorithm.

11. The method as recited in claim 10 in which step a) includes acquiring at least one image data set that samples k-space in satisfaction of a Nyquist criterion, and reconstructing a prior image from the at least one image data set.

12. The method as recited in claim 11 in which the prior image is used to initialize the expectation-maximization algorithm.

13. A method for reconstructing images of a subject from medical image data acquired with a medical imaging system, the steps of the method comprising:
   a) acquiring at least two medical image data sets with at least one medical imaging system, each of the at least two medical image data sets being acquired with a selected contrast characteristic;
   b) estimating from the at least two medical image data sets, hyperparameters related to a prior distribution of image gradient coefficients;
   c) producing a posterior distribution of image gradients using the estimated hyperparameters and the at least two medical image data sets; and
   d) reconstructing images of the subject using the produced posterior distribution of image gradients.

14. The method as recited in claim 13 in which the at least one medical imaging system includes at least one of a magnetic resonance imaging system, a computed tomography system, an x-ray imaging system, a positron emission tomography system, an ultrasound system, an optical imaging system, an electroencephalography system, and a magnetoencephalography system.

15. The method as recited in claim 14 in which the at least one medical imaging system is a magnetic resonance imaging system and the selected contrast characteristic is at least one of a $T_1$-weighting, a $T_2$-weighting, a $T^*_2$-weighting, a $T_{1\rho}$-weighting, a$T_{2\rho}$-weighting, a proton density weighting, and a diffusion weighting.

16. The method as recited in claim 14 in which the at least one medical imaging system is at least one of a computed tomography system and an x-ray imaging system, and the selected contrast characteristic is at least one of an x-ray energy level and an x-ray tube current.

17. The method as recited in claim 13 in which the hyperparameters are estimated in step b) by maximizing a log likelihood.

18. The method as recited in claim 13 in which the prior distribution of image gradient coefficients is a Gamma distribution.

19. The method as recited in claim 13 in which step d) includes deriving image gradients from the posterior distribution of image gradients.

20. The method as recited in claim 19 in which step d) includes producing transformed image gradients by performing a Fourier transform on the derived image gradients.

21. The method as recited in claim 20 in which step d) includes producing at least two refined image data sets using the transformed image gradients.

22. The method as recited in claim 21 in which the images of the subject are reconstructed by performing a Fourier transform on the at least two refined image data sets.

23. The method as recited in claim 13 in which the hyperparameters are estimated in step b) using an expectation-maximization algorithm.

24. A method for reconstructing images of a subject from image data acquired with a magnetic resonance imaging (MRI) system, the steps of the method comprising:
   a) acquiring at least two image data sets with the MRI system, wherein the at least two medical image data sets are selected from the group consisting of a structural data set, a spectroscopic data set, a functional MRI (fMRI) data set, a contrast-enhanced angiography data set, a non-contrast enhanced angiography data set, a velocity-encoded data set, a phase data set, and a magnitude data set;
   b) estimating from the at least two image data sets, hyperparameters related to a prior distribution of image gradient coefficients;
   c) producing a posterior distribution of image gradients using the estimated hyperparameters and the at least two image data sets; and
   d) reconstructing images of the subject using the produced posterior distribution of image gradients.

* * * * *